(12) United States Patent
Inagi et al.

(10) Patent No.: US 6,429,228 B1
(45) Date of Patent: *Aug. 6, 2002

(54) LOCAL ANESTHETIC FOR EXTERNAL USE

(75) Inventors: Toshio Inagi, Mishima; Akira Mada, Ihara-gun, both of (JP)

(73) Assignee: Kowa Company, Ltd., Aichi (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/284,124

(22) PCT Filed: Oct. 6, 1997

(86) PCT No.: PCT/JP97/03567

§ 371 (c)(1),
(2), (4) Date: Apr. 6, 1999

(87) PCT Pub. No.: WO98/16212

PCT Pub. Date: Apr. 23, 1998

(30) Foreign Application Priority Data

Oct. 14, 1996 (JP) ............................................. 8-270813

(51) Int. Cl.⁷ ..................... A61K 31/165; A61K 47/10; A61K 47/12
(52) U.S. Cl. ...................... 514/558; 514/617; 514/619; 514/620; 514/626; 514/817; 514/944; 514/947
(58) Field of Search ................................. 514/558, 617, 514/619, 620, 626, 817, 944, 947

(56) References Cited

U.S. PATENT DOCUMENTS

| 4,748,022 A | | 5/1988 | Busciglio |
| 4,954,487 A | * | 9/1990 | Cooper et al. ............... 514/159 |
| 5,209,724 A | | 5/1993 | Dhaliwal |
| 5,378,730 A | * | 1/1995 | Lee et al. ................... 514/535 |
| 5,580,901 A | | 12/1996 | Boardman |

FOREIGN PATENT DOCUMENTS

| JP | 82 86701 E | 9/1982 |
| JP | 43 34327 | 11/1992 |
| JP | 4-334327 | 11/1992 |
| JP | 6040947 | 2/1994 |
| JP | 94 094891 | 2/1994 |

* cited by examiner

*Primary Examiner*—Frederick Krass
(74) *Attorney, Agent, or Firm*—Kilpatrick Stockton LLP

(57) ABSTRACT

A local anesthetic for external use is prepared by blending a) an active ingredient selected from lidocaine, prilocaine, and pharmaceutically acceptable salts thereof; b) a percutaneous absorption accelerator, c) ethanol and/or isopropyl alcohol, and d) water, such that the blending ratio of ethanol and/or isopropyl alcohol to water is 0.5 to 1.2 by weight, and the pH is 6.0 to 8.5.

4 Claims, 1 Drawing Sheet

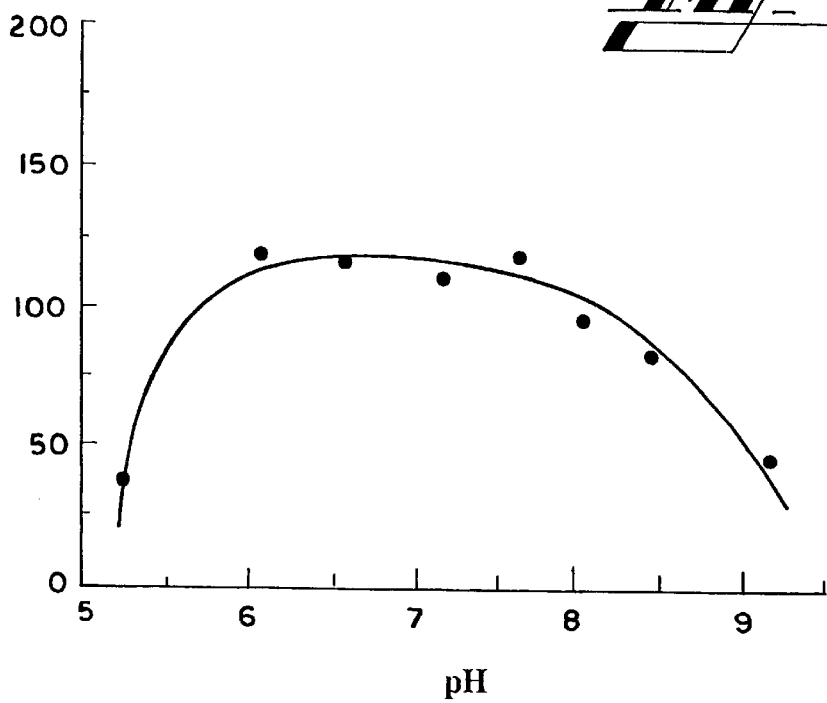
Fig_1
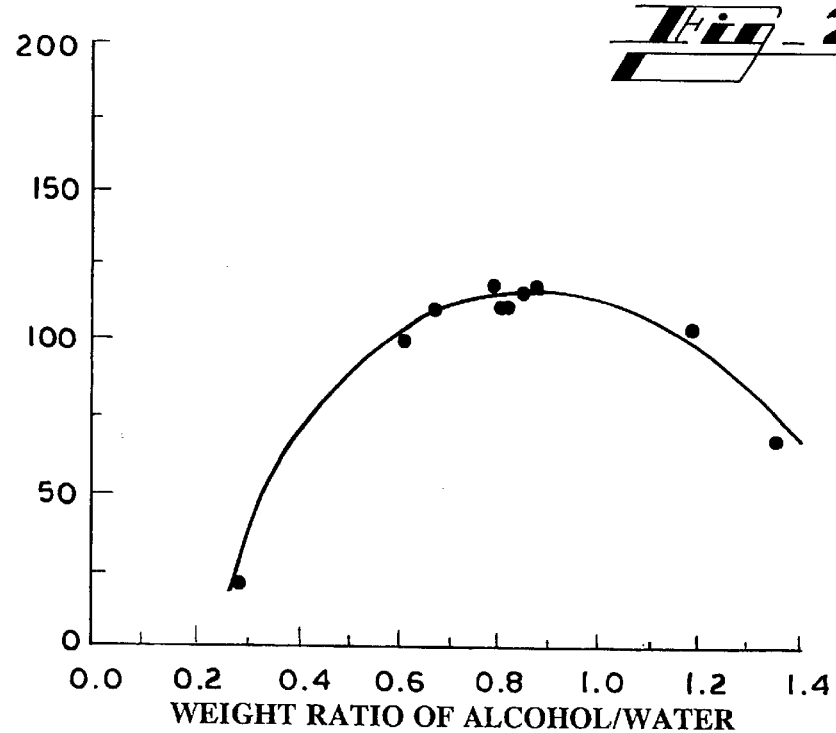
Fig_2

LOCAL ANESTHETIC FOR EXTERNAL USE

This application is a 371 of PCT/JP97/03567, filed Oct. 6, 1997.

TECHNICAL FIELD

The present invention relates to a local anesthetic for external use. In particular, the present invention relates to a local anesthetic for external use, which is conveniently usable and applicable to a broad skin surface, and which is excellent in percutaneous absorption and quick efficacy as well as excellent in stability.

BACKGROUND ART

The percutaneous absorption type local anesthetic for external use has advantages in that, for example, it does not require any special technique upon administration, it does not cause any pain, and it makes it possible to anesthetize a broad skin surface, as compared with other types of anesthetics administrated by injections such as cuteneous or subcuteneous injections. Accordingly, the percutaneous absorption type local anesthetic for external use has been considerably investigated (Japanese Laid-Open Patent Publication Nos. 57-81408, 4-305523, and 6-40947). In medical facilities such as hospitals, the local anesthetic for external use is sometimes used in accordance with a method in which an active anesthetic ingredient is blended with, for example, an agent of ointment, cream, or gel to prepare a nosocomial or clinically formulated local anesthetic which is tightly sealed, upon administration, with an extremely air-tight resin film such as a polyvinylidene chloride film ("ODT method"; Hifu, 34 (2), 237–242 (1992)). Recently, a tape-shaped medicament has been developed, and it has been commercially available for medical use.

However, the following problems have been pointed out for the conventional pharmaceutical preparations. Namely, any of the pharmaceutical preparations described in the respective patent documents is insufficient in percutaneous absorption and quick efficacy. As for the nosocomial local anesthetic pharmaceutical preparations formulated, for example, as the ointment, the cream, or the gel form agent, some of the pharmaceutical preparations have poor stability, and hence it is necessary for such pharmaceutical preparations to be prepared when they are used. Further, other of the pharmaceutical preparations are inconvenient for use, and they require a long time to express the anesthetic effect. Moreover, the tape-shaped medicament is unsuitable to anesthetize a broad skin surface. Although the anesthetic is blended at a high concentration (30 to 60%), the tape-shaped medicament is deficient in percutaneous absorption and quick efficacy.

DISCLOSURE OF THE INVENTION

The present invention has been made taking the foregoing viewpoints into consideration, an object of which is to provide a percutaneous absorption type local anesthetic for external use which is conveniently used when it is applied and peeled off, which is applicable to a broad skin surface, and which is excellent in percutaneous absorption and quick efficacy as well as excellent in stability.

As a result of diligent investigations performed by the present inventors in order to achieve the object described above, it has been found that when an active ingredient selected from lidocaine, prilocaine, and pharmaceutically acceptable salts thereof is allowed to be contained in a mixed solution comprising water and lower alcohol such as ethanol and isopropyl alcohol, and a resultant solution is allowed to further contain a percutaneous absorption accelerator to formulate a pharmaceutical preparation so that it is used as a percutaneous absorption type local anesthetic, then it is possible to improve the percutaneous absorption of the active ingredient and shorten the time required to express the anesthetic effect, and the pharmaceutical preparation containing the foregoing components is excellent in stability. Thus the present invention has been completed.

Namely, the present invention lies in a local anesthetic for external use, containing a) an active ingredient selected from lidocaine, prilocaine, and pharmaceutically acceptable salts thereof, b) a percutaneous absorption accelerator, c) ethanol and/or isopropyl alcohol, and d) water.

Specifically, the b) percutaneous absorption accelerator contained in the local anesthetic for external use of the present invention preferably includes fatty acids each having a number of carbon atoms of 8 to 18 and pharmaceutically acceptable salts thereof. Among these compounds, those more preferably used include caprylic acid having a number of carbon atoms of 8, oleic acid having a number of carbon atoms of 18, and pharmaceutically acceptable salts thereof.

Specifically, the local anesthetic for external use of the present invention contains c) ethanol and/or isopropyl alcohol and d) water preferably in a ratio of content within a range of 0.5 to 1.2 as expressed by a weight ratio of ethanol and/or isopropyl alcohol to water. The local anesthetic for external use of the present invention preferably has a pH within a range of 6.0 to 8.5.

As for the form of agent, for example, the local anesthetic for external use of the present invention is preferably applied as a gel form agent.

The present invention will be explained in detail below.

The local anesthetic for external use of the present invention contains a) the active ingredient selected from lidocaine, prilocaine, and pharmaceutically acceptable-salts thereof, b) the percutaneous absorption accelerator, c) ethanol and/or isopropyl alcohol, and d) water. The foregoing respective components a) to d) will be successively explained below.

a) Lidocaine, Prilocaine, and Pharmaceutically Acceptable Salts Thereof

Both of lidocaine and prilocaine are compounds known as local anesthetics. These compounds are easily obtained by chemical synthesis. Therefore, chemically synthesized products known as described above can be used for the local anesthetic for external use of the present invention. In general, these compounds are commercially available. Therefore, it is also possible to use commercially available products in the present invention. The local anesthetic for external use of the present invention contains, as the active ingredient, lidocaine or prilocaine singly, or a mixture of them. However, the local anesthetic for external use of the present invention can contain one or more pharmaceutically acceptable salts of lidocaine and prilocaine in place of them or in addition to them. The pharmaceutically acceptable salts specifically include, for example, hydrochloride of lidocaine and hydrochloride of prilocaine.

In the local anesthetic for external use of the present invention, the content of the active ingredient selected from lidocaine, prilocaine, and pharmaceutically acceptable salts thereof is preferably about 2 to 12% by weight, and more preferably 5 to 10% by weight with respect to the total amount of the pharmaceutical preparation, however, the content of the active ingredient varies depending on the type or form of agent, the position at which the agent is used, and the method with which the agent is used.

b) Percutaneous Absorption Accelerator

The percutaneous absorption accelerator contained in the local anesthetic for external use of the present invention is not specifically limited provided that the absorption accelerator has a function to accelerate percutaneous absorption of lidocaine, prilocaine, and pharmaceutically acceptable salts thereof as the active ingredient of the local anesthetic for external use of the present invention, and that the absorption accelerator is a pharmaceutically acceptable compound. Specifically, those preferably used as the percutaneous absorption accelerator include fatty acids each having a number of carbon atoms of 8 to 18 and pharmaceutically acceptable salts thereof. The fatty acid having a number of carbon atoms of 8 to 18 includes, for example, caprylic acid, capric acid, myristic acid, palmitic acid, stearic acid, oleic acid, linoleic acid, and linolenic acid. Among these compounds, those more preferably used for the local anesthetic for external use of the present invention are exemplified by caprylic acid having a number of carbon atoms of 8, and oleic acid having a number of carbon atoms of 18. The pharmaceutically acceptable salts of these fatty acids may include, for example, sodium salts, potassium salts, calcium salts, aluminum salts, and zinc salts.

The content of the percutaneous absorption accelerator of the local anesthetic for external use of the present invention is preferably about 1.0 to 7.0% by weight, and more preferably 2.0 to 4.0% by weight with respect to the total amount of the pharmaceutical preparation, when the fatty acids each having a number of carbon atoms of 8 to 18 or the pharmaceutically acceptable salts thereof are used as the percutaneous absorption accelerator, however, the content of the percutaneous absorption accelerator varies depending on, for example, the type and the content of the active ingredient.

c) Ethanol and/or Isopropyl Alcohol, and d) Water

The local anesthetic for external use of the present invention comprises ethanol and/or isopropyl alcohol and water which are contained as base materials in the local anesthetic for external use. The ratio of ethanol and/or isopropyl alcohol to water, mixed and contained as the base materials in the local anesthetic for external use of the present invention, is preferably within a range of 0.5 to 1.2, and more preferably within a range of 0.6 to a 1.2, as expressed by the weight ratio of ethanol and/or isopropyl alcohol to water.

The total content of ethanol and/or isopropyl alcohol and water, i.e., the content of the base materials in the local anesthetic for external use of the present invention is preferably about 59 to 90% by weight, and more preferably 72 to 80 % by weight with respect to the total amount of the pharmaceutical preparation, however, the total content of ethanol and/or isopropyl alcohol and water varies depending on, for example, the types and the contents of the active ingredient and the percutaneous absorption accelerator.

The local anesthetic for external use of the present invention contains the respective components a) to d) as described above. However, the local anesthetic for external use of the present invention may further contain arbitrary components generally contained in ordinary local anesthetics for external use, if necessary, provided that the arbitrary components are contained within a range in which the effect of the present invention is not deteriorated. Such an arbitrary component is firstly exemplified by a pH-adjusting agent. Considering the viewpoint of the percutaneous absorption, the local anesthetic for external use of the present invention preferably has a pH within a range of about 6.0 to 8.5, and more preferably within a range of 6.0 to 8.0. In order to adjust pH to be within the preferred range described above, the local anesthetic for external use of the present invention may contain one or more agents selected from various pH-adjusting agents including, for example, hydrochloric acid, lactic acid, diisopropanolamine, and triethanolamine. The content of the pH-adjusting agent is preferably not more than 8.0% by weight, and more preferably 0.05 to 5.5% by weight with respect to the total amount of the pharmaceutical preparation.

Besides the pH-adjusting agent described above, the arbitrary component, which may be contained in the local anesthetic for external use of the present invention, may be exemplified by components appropriately contained in conformity with various types or forms of agents to which the local anesthetic for external use of the present invention is applicable. The type or form of agent, to which the local anesthetic for external use of the present invention is applicable, includes, for example, agents of the form of ointment, cream, gel, liquid, poultice, and plaster. However, the type or form of agent of the local anesthetic for external use of the present invention is preferably a gel form agent. Those usable as the arbitrary components appropriately contained in conformity with the various types or forms of agents may be used within a range in which the effect of the present invention is not deteriorated.

For example, when the local anesthetic for external use of the present invention is the gel form agent which is preferred in the present invention, those usable as the arbitrary components include, for example, polyvalent alcohol and high molecular weight additives such as polyvinyl alcohol and cellulose derivatives. Those usable as polyvinyl alcohol preferably include those having a molecular weight of about 1700 to 2400. Those usable as the cellulose derivative include, for example, sodium carboxymethyl cellulose, hydroxypropyl cellulose, and hydroxypropylmethyl cellulose. Specifically, those usable as the polyvalent alcohol may include, for example, glycerol, propylene glycol, 1,3-butanediol, and polyethylene glycol.

A coloring agent such as a tar dye can be added to the local anesthetic for external use of the present invention, regardless of the type or form of agent, if necessary. Accordingly, it is possible to obtain a colored pharmaceutical preparation. Specifically, those usable as the coloring agent include coloring materials prescribed by the Pharmaceutical Affairs Law. Such coloring materials include, as the tar dye, for example, Amaranth, New Coccine, Phloxine B. and Rose Bengale.

The method for producing the local anesthetic for external use of the present invention may include ordinary production methods to be used corresponding to the various types or forms of agents to which the local anesthetic for external use of the present invention is applied. Specifically, for example, when the local anesthetic for external use of the present invention is produced as the gel form agent which is a preferred type or form of agent for the local anesthetic for external use of the present invention, the following method can be exemplified. However, the present invention is not limited to the following method for producing the local anesthetic for external use.

At first, the percutaneous absorption accelerator and the active ingredient selected from lidocaine, prilocaine, and pharmaceutically acceptable salts thereof are dissolved in a mixed solution comprising ethanol and/or isopropyl alcohol and water. Alternatively, the active ingredient and the percutaneous absorption accelerator are separately dissolved in ethanol and/or isopropyl alcohol, or water, or a mixed solution thereof respectively, and obtained respective solutions are mixed with each other. After that, a solution obtained by dissolving a gelling agent such as a high molecular weight additive or polyvalent alcohol in ethanol and/or isopropyl alcohol, water, or a mixed solution thereof is mixed with the foregoing solution containing the active ingredient and the percutaneous absorption accelerator to obtain a gel form agent. During this process, it is also possible to add beforehand a part of the active ingredient and/or a part of the percutaneous absorption accelerator to the solution of the gelling agent, if necessary. During the foregoing dissolving process and/or the mixing process, it is allowable to perform, for example, heating and agitation. Further, during the dissolving process and/or the mixing process performed in the production method described above, it is possible to add the arbitrary components such as the pH-adjusting agent, the coloring agent, polyvalent alcohol, and perfumes, if necessary.

The local anesthetic for external use of the present invention obtained as described above is less stimulus to skin, and it can be applied to a broad skin surface, while having a sufficient adsorptive force to skin. Accordingly, the local anesthetic for external use of the present invention is excellent and convenient for use such that, for example, it can be easily applied, while it can be conveniently peeled off. The local anesthetic for external use of the present invention forms a coating when it is used. Therefore, the active ingredient is percutaneously absorbed well, and it is possible to express the anesthetic effect within a short period of time. Further, the local anesthetic for external use of the present invention is excellent in stability when it is formulated to be a pharmaceutical preparation.

BRIEF DESCRIPTION OF THE DRAWINGS

FIG. 1 shows a relationship between the pH value and the amount of percutaneously absorbed lidocaine ($\mu g/cm^2$), concerning the gel form agent containing lidocaine prepared according to the present invention.

FIG. 2 shows a relationship between the weight ratio of alcohol/water and the amount of percutaneously absorbed lidocaine ($\mu g/cm^2$), concerning the gel form agent containing lidocaine prepared according to the present invention.

BEST MODE FOR CARRYING OUT THE INVENTION

The present invention will be more specifically explained below with reference to Examples.

EXAMPLES 1 to 16

Local anesthetics for external use, i.e., lidocaine gels were produced by using components formulated as shown in Table 1. Namely, a solution (Solution A) was produced by dissolving or suspending and mixing respective components of the group A, and a solution (Solution B) was produced by warming and dissolving or suspending respective components of the group B. Solution A was added to Solution B obtained as described above, followed by agitation to obtain a homogeneous mixture. The homogeneous mixture was added with respective components of the group C, followed by agitation and homogenization to produce the gel form agent. After that, pH was measured for the obtained respective gel form agents. The weight ratio (hereinafter referred to as "weight ratio of alcohol/water", if necessary) of alcohol (ethanol and/or isopropyl alcohol) to contained water was determined for the obtained respective gel form agents. The weight ratio of alcohol/water is shown in the middle part of Table 1, together with pH.

TABLE 1

| Component | Blending amount (% by weight) Example |||||||||||||||| |
| --- | --- | --- | --- | --- | --- | --- | --- | --- | --- | --- | --- | --- | --- | --- | --- | --- |
| | 1 | 2 | 3 | 4 | 5 | 6 | 7 | 8 | 9 | 10 | 11 | 12 | 13 | 14 | 15 | 16 |
| A | | | | | | | | | | | | | | | | |
| Lidocaine | 5.0 | 10.0 | 10.0 | 10.0 | 10.0 | 10.0 | 10.0 | 10.0 | 10.0 | 10.0 | 10.0 | 5.0 | 10.0 | 10.0 | 10.0 | 10.0 |
| Oleic acid | — | 0.8 | 0.6 | 0.8 | 0.8 | 0.8 | 0.8 | 0.8 | 0.8 | 0.5 | — | 2.0 | 0.8 | 0.8 | 2.0 | 3.0 |
| Ethanol | 33.0 | — | 33.0 | 33.0 | 33.0 | 33.0 | 33.0 | 33.0 | 33.0 | — | 42.0 | 15.0 | 33.0 | 33.0 | 10.0 | 44.0 |
| Isopropyl alcohol | — | 30.0 | — | — | — | — | — | — | — | 28.0 | — | — | — | — | — | — |
| B | | | | | | | | | | | | | | | | |
| Sodium caprylate | 2.4 | 2.4 | 2.6 | 2.4 | 2.4 | 2.4 | 2.4 | 2.4 | 2.4 | 3.0 | 2.0 | — | 2.4 | 2.4 | 2.0 | — |
| Polyvinyl alcohol | 10.0 | 10.0 | 10.0 | 10.0 | 10.0 | 10.0 | 10.0 | 10.0 | 10.0 | 10.0 | 10.0 | 20.0 | 10.0 | 10.0 | 10.0 | 10.0 |
| Sodium carboxymethyl cellulose | 1.0 | — | — | — | — | — | — | — | — | — | — | — | — | — | — | — |
| Purified water | 48.53 | 46.6 | 41.6 | 38.4 | 40.0 | 41.4 | 42.6 | 43.4 | 41.2 | 47.5 | 35.8 | 58.0 | 36.6 | 39.2 | 64.5 | 32.9 |
| C | | | | | | | | | | | | | | | | |
| Hydrochloric acid | 0.07 | 0.2 | — | — | — | — | — | — | — | — | 0.2 | — | — | — | — | 0.1 |
| Lactic acid | — | — | 2.2 | 5.4 | 3.8 | 2.4 | 1.2 | 0.4 | 0.6 | 1.0 | — | — | 7.2 | — | 1.5 | — |
| Triethanolamine | — | — | — | — | — | — | — | — | 2.0 | — | — | — | — | 4.6 | — | — |
| Weight ratio of alcohol/water | 0.68 | 0.64 | 0.79 | 0.86 | 0.83 | 0.80 | 0.77 | 0.76 | 0.80 | 0.59 | 1.17 | 0.26 | 0.90 | 0.84 | 0.16 | 1.34 |
| pH | 8.0 | 6.2 | 7.1 | 6.0 | 6.5 | 7.1 | 7.6 | 8.0 | 8.4 | 7.7 | 7.8 | 7.7 | 5.2 | 9.1 | 7.3 | 7.5 |
| Evaluation | | | | | | | | | | | | | | | | |
| Anesthetic effect (%) | 83 | 100 | 100 | 100 | 100 | 100 | 100 | 100 | 83 | 100 | 100 | 0 | 33 | 33 | 17 | 50 |
| Absorption amount ($\mu g/cm^2$) | 71 | 107 | 108 | 115 | 113 | 108 | 115 | 93 | 80 | 97 | 102 | 17 | 34 | 43 | 25 | 66 |

COMPARATIVE EXAMPLE

A local anesthetic for external use, i.e., lidocaine cream, which was equivalent to those hitherto used as a nosocomial pharmaceutical preparation, was produced as Comparative Example by using components formulated as shown in Table 2.

Namely, components of the group A shown in Table 2 were sufficiently mixed to obtain a mixture which was then homogeneously incorporated with a component of the group B to produce the lidocaine cream. Sonne Base used as the B component is an ointment base material of emulsive lotion made by SONYBOD PHARMACEUTICAL CO., LTD, comprising blended components of glycerol monostearate, stearyl alcohol, cetanol, light anhydrous silicic acid, cetaceum, propylene glycol, polyoxyethylene cetyl ether, and purified water.

TABLE 2

| Component | Blended amount (% by weight) |
|---|---|
| <A> Lidocaine | 10.0 |
| Glycerol | 30.0 |
| <B> Sonne Base | 60.0 |
| Evaluation | |
| Anesthetic effect (%) | 33 |
| Absorption amount ($\mu$g/cm$^2$) | 30 |

<Evaluation of Local Anesthetic for External Use of the Present Invention>

The pharmaceutical preparations of the local anesthetics for external use containing lidocaine obtained in Examples and Comparative Example respectively were evaluated by performing tests for anesthetic effect, percutaneous absorption, and stability in accordance with the following methods.

(1) Anesthetic Effect Test

Hairs were removed by means of shaving (depilatory agent was also used) from Hartley type guinea pigs (four weeks old, male). The pharmaceutical preparation (0.75 g) was homogeneously applied to a back portion (9 cm$^2$, 3 cm×3 cm) of each of the guinea pigs. The pharmaceutical preparation was peeled off 30 minutes after the application. After the pharmaceutical preparation was peeled off, the back portion, on which the pharmaceutical preparation had been applied, was stimulated six times with a mandolin wire to observe the presence or absence of the contraction reaction of skin. The number of times without any observation of the contraction reaction was represented by percentage (%) as a ratio with respect to the total number of times (six times). The percentage was regarded as the anesthetic effect. The anesthetic effect test was performed by using two guinea pigs for each of the pharmaceutical preparations to determine an average thereof.

(2) Percutaneous Absorption Test

After completion of the anesthetic effect test, the back portion, on which the pharmaceutical preparation had been applied, was sufficiently wiped with cotton immersed with alcohol for all of the guinea pigs. After that, the skin (4 cm$^2$, 2 cm×2 cm) corresponding to the central portion was excised. The concentration of the local anesthetic or salt thereof contained in the excised skin was determined in accordance with a high-performance liquid chromatography method (HPLC method) to calculate the absorption amount per unit area ($\mu$g/cm$^2$). An average of the values obtained for two guinea pigs subjected to the foregoing test was determined for each of the pharmaceutical preparations.

Results of (1) the anesthetic effect test and (2) the percutaneous absorption test are shown in the lowest parts in Tables 1 and 2. A graph (FIG. 1) was obtained for the relationship between the pH value of the lidocaine gel agent of the present invention and the amount of percutaneously absorbed lidocaine ($\mu$g/cm$^2$) in guinea pigs, from the results of the percutaneous absorption test for each of the lidocaine gel agents obtained in Examples. Similarly, a graph (FIG. 2) was obtained for the relationship between the weight ratio of alcohol/water of the lidocaine gel agent of the present invention and the amount of percutaneously absorbed lidocaine ($\mu$g/cm$^2$) in guinea pigs.

As clarified from the results, it is understood that when the lidocaine gel agent obtained in each of Examples was administrated to guinea pigs, the amount of percutaneously absorbed lidocaine obtained 30 minutes after the application was large, and the anesthetic effect was excellent aptitudinally, as compared with the lidocaine cream obtained in Comparative Example. When the results are compared with the test result obtained by the ODT method for the lidocaine cream having been hitherto used as the nosocomial pharmaceutical preparation, the lidocaine cream having approximately the same composition as that of the lidocaine cream obtained in Comparative Example, i.e., the fact that it takes about 2 hours to obtain a sufficient anesthetic effect after application of the cream (Hifu, 34 (2), 237–242 (1992)), it can be confirmed that the time required to express the anesthetic effect is extremely short in the case of the local anesthetic for external use of the present invention. Further, concerning the lidocaine gel agents obtained in Examples, it was revealed that the lidocaine gel agents, in which the weight ratio of alcohol/water was within a range of 0.5 to 1.2, or pH was within a range of 6 to 8.5, were especially excellent in the percutaneous absorption amount and in the anesthetic effect.

The lidocaine gel agents, which were obtained in respective Examples concerning the tests based on the use of guinea pigs, were extremely conveniently used, for example, when they are applied and peeled off. Thus it has been confirmed that the local anesthetic for external use of the present invention can be used in a convenient manner.

(3) Stability Test

The lidocaine gel agents obtained in Example 1 and Examples 5 to 10 were placed in glass vials respectively, and they were tightly sealed. After that, they were stored for 1 month in a thermostat tank at 50° C. After 1 month, all of the glass vials were taken out of the thermostat tank, and they were opened to observe the presence or absence of any change in appearance (discoloration and separation) for the respective lidocaine gel agents. The lidocaine content was measured by means of the high-performance liquid chromatography method (HPLC method) for the respective lidocaine gel agents after being stored at 50° C. for 1 month to determine the percentage of the lidocaine content after the storage at 50° C. for 1 month with respect to the lidocaine content upon the formulation of the pharmaceutical preparations. The percentage was regarded as the remaining ratio (%) of lidocaine. Results of the evaluation are shown in Table 3.

TABLE 3

| | Example No. | | | | | | |
|---|---|---|---|---|---|---|---|
| Evaluation item | 1 | 5 | 6 | 7 | 8 | 9 | 10 |
| Presence or absence of change in appearance | | | | | | | |
| Discoloration | no | no | no | no | no | no | no |
| Separation | no | no | no | no | no | no | no |
| Remaining ratio of lidocaine (%) | 98 | 98 | 98 | 99 | 100 | 98 | 100 |

As clarified from the results, no change in appearance was observed, i.e., neither discoloration nor separation was observed for the lidocaine gel agents obtained in respective Examples, after being stored under the severe condition at 50° C. for 1 month. Lidocaine blended in the pharmaceutical preparation upon the formulation remained in the pharmaceutical preparation at the remaining ratio of about 100% after the storage under the foregoing condition, in the case of any of the lidocaine gel agents obtained in Examples described above. Therefore, it is acknowledged that the local anesthetic for external use of the present invention is also extremely excellent in stability.

INDUSTRIAL APPLICABILITY

The percutaneous absorption type local anesthetic for external use of the present invention is conveniently used when it is applied and peeled off, it is applicable to a broad skin surface, and it is excellent in percutaneous absorption and quick efficacy as well as excellent in stability.

What is claimed is:

1. A local anesthetic for external use, consisting essentially of, a) an active ingredient selected from lidocaine, prilococaine, or pharmaceutically acceptable salts thereof;
   b) a percutaneous absorption accelerator selected from fatty acids each having a number of carbon atoms of 8 to 18 or pharmaceutically acceptable salts thereof;
   c) ethanol and/or isopropyl alcohol; and
   d) water, wherein the ratio of ethanol and/or isopropyl alcohol to water is within the range of 0.5 to 1.2 as expressed in weight, and the pH of the anesthetic is within the range of approximately 6.0 to 8.5.

2. The anesthetic of claim 1, wherein the anesthetic is a gel.

3. The anesthetic of claim 1, wherein the fatty acid is capryllic acid or oleic acid.

4. The anesthetic of claim 3, wherein the anesthetic is a gel.

* * * * *